US009636306B2

(12) United States Patent
Odidi et al.

(10) Patent No.: US 9,636,306 B2
(45) Date of Patent: May 2, 2017

(54) PROTON PUMP-INHIBITOR-CONTAINING CAPSULES WHICH COMPRISE SUBUNITS DIFFERENTLY STRUCTURED FOR A DELAYED RELEASE OF THE ACTIVE INGREDIENT

(71) Applicants: Isa Odidi, Toronto (CA); Amina Odidi, Toronto (CA)

(72) Inventors: Isa Odidi, Toronto (CA); Amina Odidi, Toronto (CA)

(73) Assignee: INTELLIPHARMACEUTICS CORP., Toronto, Ontario (CA)

( * ) Notice: Subject to any disclaimer, the term of this patent is extended or adjusted under 35 U.S.C. 154(b) by 159 days.

(21) Appl. No.: 14/327,701

(22) Filed: Jul. 10, 2014

(65) Prior Publication Data
US 2014/0322312 A1 Oct. 30, 2014

Related U.S. Application Data

(62) Division of application No. 10/561,700, filed as application No. PCT/CA2004/000825 on Jun. 3, 2004, now Pat. No. 8,802,139.

(60) Provisional application No. 60/482,439, filed on Jun. 26, 2003, provisional application No. 60/548,903, filed on Mar. 2, 2004.

(51) Int. Cl.
| | |
|---|---|
| *A61K 9/48* | (2006.01) |
| *A61K 9/20* | (2006.01) |
| *A61K 9/28* | (2006.01) |
| *A61K 31/00* | (2006.01) |
| *A61K 31/44* | (2006.01) |
| *A61K 31/4439* | (2006.01) |
| *A61K 45/06* | (2006.01) |
| *A61K 31/4184* | (2006.01) |
| *A61K 31/435* | (2006.01) |
| *A61K 9/16* | (2006.01) |
| *A61K 9/50* | (2006.01) |

(52) U.S. Cl.
CPC .......... *A61K 9/4808* (2013.01); *A61K 9/2018* (2013.01); *A61K 9/2027* (2013.01); *A61K 9/2054* (2013.01); *A61K 9/2846* (2013.01); *A61K 9/2866* (2013.01); *A61K 9/2886* (2013.01); *A61K 9/48* (2013.01); *A61K 9/5084* (2013.01); *A61K 31/00* (2013.01); *A61K 31/4184* (2013.01); *A61K 31/435* (2013.01); *A61K 31/44* (2013.01); *A61K 31/4439* (2013.01); *A61K 45/06* (2013.01); *A61K 9/1635* (2013.01); *A61K 9/1652* (2013.01); *A61K 9/5026* (2013.01)

(58) Field of Classification Search
CPC .. A61K 9/2054; A61K 9/2866; A61K 9/2886; A61K 9/48; A61K 9/4808
See application file for complete search history.

(56) References Cited

U.S. PATENT DOCUMENTS

| | | |
|---|---|---|
| 2,540,979 A | 2/1951 | Macdonnell |
| 3,254,088 A | 5/1966 | Juda et al. |
| 3,493,657 A | 2/1970 | Lewenstein |
| 3,629,393 A | 12/1971 | Nakamoto et al. |
| 3,728,445 A | 4/1973 | Bardani |
| 3,773,955 A | 11/1973 | Pachter |
| 3,789,117 A | 1/1974 | Tsujino |
| 3,819,706 A | 6/1974 | Mehta |
| 3,845,770 A | 11/1974 | Higuchi |
| 3,856,721 A | 12/1974 | Fritschell |
| 3,916,899 A | 11/1975 | Theeuwes et al. |
| 4,008,719 A | 2/1977 | Theeuwes |
| 4,016,880 A | 4/1977 | Theeuwes |
| 4,034,758 A | 7/1977 | Theeuwes |
| 4,036,228 A | 7/1977 | Theeuwes |

(Continued)

FOREIGN PATENT DOCUMENTS

| | | |
|---|---|---|
| CA | 2286684 A1 | 10/1998 |
| CA | 2539984 A1 | 12/2004 |

(Continued)

OTHER PUBLICATIONS

Supplemental European Search Report Prepared by Miralles J. Gimerez Aug. 23, 2012 Supplemental European Search Report Prepared by Antonio Raposo Aug. 2, 2012.
Torpac, Capsul Size Chart, 2000, pp. 1-3.
Anderson, M. et al., Analysis of Film Coating Thickness and Surface Area of Pharmaceutical Pellets using Fluorescence Microscopy and Image Analysis, J. Pharmaceutical and Biomedical Analysis, (2000), vol. 22, pp. 325-339.
Arora, S. et al, Pulsatie Drug Delivery Systems: An Approach for Controlled Drug Delivery, Indian J. Pham. Sc., (2006), vol. 68, pp. 295-300.

(Continued)

Primary Examiner — Kyle Purdy
(74) Attorney, Agent, or Firm — Thomas Horstemeyer, LLP

(57) ABSTRACT

An oral pharmaceutical composition comprises multiple populations of at least one of beads, pellets, tablets and granules provided in a capsule, the composition comprising: a first population of a pharmaceutical active comprising a pharmaceutical active substance releasable at a first rate; a population of a basic substance; and a second population of a pharmaceutical active comprising a pharmaceutical active substance releasable at a second rate. In another embodiment, the oral pharmaceutical composition comprises multiple populations of at least one of beads, pellets, tablets and granules provided in a capsule, the composition comprising: a population of a pharmaceutical active; a population of a basic substance; a population of enteric coated pharmaceutical active; and a population of enteric coated basic substance. The composition can provide multiple site specific delivery of a pharmaceutical active in a rapid, delayed and/or sustained release manner into the plasma.

41 Claims, No Drawings

(56) References Cited

U.S. PATENT DOCUMENTS

| | | |
|---|---|---|
| 4,045,563 A | 8/1977 | Berntsson et al. |
| 4,060,598 A | 11/1977 | Groppenbacher et al. |
| 4,077,407 A | 3/1978 | Theeuwes |
| 4,160,452 A | 7/1979 | Theeuwes |
| 4,161,477 A | 7/1979 | Long |
| 4,183,838 A | 1/1980 | Gagliani |
| 4,183,839 A | 1/1980 | Gagliani |
| 4,193,985 A | 3/1980 | Bechgaard |
| 4,200,098 A | 4/1980 | Ayer |
| 4,218,433 A | 8/1980 | Kooichi et al. |
| 4,248,856 A | 2/1981 | Guley et al. |
| 4,250,136 A | 2/1981 | Rex |
| 4,252,786 A | 2/1981 | Weiss et al. |
| 4,255,431 A | 3/1981 | Junggren et al. |
| 4,309,405 A | 1/1982 | Guley et al. |
| 4,327,725 A | 5/1982 | Cortese |
| 4,330,338 A | 5/1982 | Banker |
| 4,337,257 A | 6/1982 | Junggren |
| 4,389,393 A | 6/1983 | Schor et al. |
| 4,425,441 A | 1/1984 | Gagliani et al. |
| 4,457,933 A | 7/1984 | Gordon |
| 4,461,759 A | 7/1984 | Dunn |
| 4,486,412 A | 12/1984 | Shah et al. |
| 4,508,905 A | 4/1985 | Junggren |
| 4,514,538 A | 4/1985 | Shvakhman et al. |
| 4,517,112 A | 5/1985 | Mardis et al. |
| 4,518,717 A | 5/1985 | Long et al. |
| 4,545,412 A | 10/1985 | Gamberini |
| 4,582,835 A | 4/1986 | Lewis |
| 4,606,909 A | 8/1986 | Bechgaard |
| 4,610,870 A | 9/1986 | Jain et al. |
| 4,612,008 A | 9/1986 | Wong et al. |
| 4,628,098 A | 12/1986 | Nohara et al. |
| 4,666,705 A | 5/1987 | Decrosta et al. |
| 4,676,929 A | 6/1987 | Rittler |
| 4,684,516 A | 8/1987 | Bhutani |
| 4,686,230 A | 8/1987 | Rainer et al. |
| 4,689,333 A | 8/1987 | Nohara et al. |
| 4,704,285 A | 11/1987 | Alderman |
| 4,708,834 A | 11/1987 | Cohen et al. |
| 4,713,248 A | 12/1987 | Kjomaes et al. |
| 4,756,911 A | 7/1988 | Drost et al. |
| 4,758,579 A | 7/1988 | Kohl et al. |
| 4,765,989 A | 8/1988 | Wong et al. |
| 4,783,337 A | 11/1988 | Wong et al. |
| 4,786,505 A | 11/1988 | Lovgren et al. |
| 4,812,446 A | 3/1989 | Brand |
| 4,818,760 A | 4/1989 | Binder et al. |
| 4,832,958 A | 5/1989 | Baudier et al. |
| 4,844,905 A | 7/1989 | Ichikawa et al. |
| 4,845,118 A | 7/1989 | Lang et al. |
| 4,851,228 A | 7/1989 | Zentner et al. |
| 4,853,230 A | 8/1989 | Lovgren et al. |
| 4,869,908 A | 9/1989 | Kirschner et al. |
| 4,880,631 A | 11/1989 | Haslam |
| 4,886,668 A | 12/1989 | Haslam |
| 4,891,223 A | 1/1990 | Ambegaonkar et al. |
| 4,892,742 A | 1/1990 | Shah |
| 4,900,557 A | 2/1990 | Dell et al. |
| 4,904,476 A | 2/1990 | Mehta et al. |
| 4,927,640 A | 5/1990 | Dahlinder et al. |
| 4,935,243 A | 6/1990 | Borkan et al. |
| 4,940,587 A | 7/1990 | Jenkins et al. |
| 4,940,588 A | 7/1990 | Sparks et al. |
| 4,946,853 A | 8/1990 | Bannon et al. |
| 4,963,365 A | 10/1990 | Samejima et al. |
| 4,965,269 A | 10/1990 | Brandstrom et al. |
| 4,966,768 A | 10/1990 | Michelucci et al. |
| 5,000,962 A | 3/1991 | Sangekar et al. |
| 5,004,614 A | 4/1991 | Staniforth |
| 5,021,433 A | 6/1991 | Alminger et al. |
| 5,028,434 A | 7/1991 | Barclay et al. |
| 5,045,552 A | 9/1991 | Souda et al. |
| 5,049,394 A | 9/1991 | Howard et al. |
| 5,071,643 A | 12/1991 | Yu et al. |
| 5,073,384 A | 12/1991 | Valentine et al. |
| 5,077,051 A | 12/1991 | Gallopo |
| 5,123,146 A | 6/1992 | Olson |
| 5,145,871 A | 9/1992 | Cavazza |
| 5,149,702 A | 9/1992 | Yamada et al. |
| 5,190,763 A | 3/1993 | Edgren et al. |
| 5,202,128 A | 4/1993 | Morella et al. |
| 5,219,572 A | 6/1993 | Sivaramakrishnan |
| 5,229,131 A | 7/1993 | Amidon et al. |
| 5,236,714 A | 8/1993 | Lee et al. |
| 5,240,712 A | 8/1993 | Smith |
| 5,252,339 A | 10/1993 | Cristofori et al. |
| 5,260,069 A | 11/1993 | Chen |
| 5,286,497 A | 2/1994 | Hendrickson et al. |
| 5,288,500 A | 2/1994 | Ibsen |
| 5,290,816 A | 3/1994 | Blumberg |
| 5,330,766 A | 7/1994 | Morella |
| 5,376,388 A | 12/1994 | Meyers |
| 5,378,474 A | 1/1995 | Morella et al. |
| 5,393,528 A | 2/1995 | Staab |
| 5,430,042 A | 7/1995 | Lindberg et al. |
| 5,445,829 A | 8/1995 | Paradissis et al. |
| 5,458,887 A | 10/1995 | Chen et al. |
| 5,472,711 A | 12/1995 | Baichwal |
| 5,480,335 A | 1/1996 | Caveza |
| 5,503,846 A | 4/1996 | Wehling |
| 5,508,040 A | 4/1996 | Chen |
| 5,527,545 A | 6/1996 | Santus et al. |
| 5,595,762 A | 1/1997 | Derrieu |
| 5,681,581 A | 10/1997 | Dunn |
| 5,708,017 A | 1/1998 | Dave et al. |
| 5,713,000 A | 1/1998 | Larson |
| 5,736,159 A | 4/1998 | Chen et al. |
| 5,753,265 A | 5/1998 | Bergstrand |
| 5,759,577 A | 6/1998 | Barcomb |
| 5,760,121 A | 6/1998 | Beall et al. |
| 5,780,055 A | 7/1998 | Habib et al. |
| 5,783,215 A | 7/1998 | Arwidsson et al. |
| 5,795,583 A | 8/1998 | Grune et al. |
| 5,800,422 A | 9/1998 | Dong et al. |
| 5,817,338 A | 10/1998 | Bergstrand |
| 5,840,329 A | 11/1998 | Bai |
| 5,840,910 A | 11/1998 | Souda et al. |
| 5,879,708 A | 3/1999 | Makino et al. |
| 5,955,106 A | 9/1999 | Moeckel et al. |
| 5,972,329 A | 10/1999 | Chuang et al. |
| 5,998,445 A | 12/1999 | Souda et al. |
| 6,022,562 A | 2/2000 | Autant et al. |
| 6,039,975 A | 3/2000 | Shah et al. |
| 6,046,177 A | 4/2000 | Stella |
| 6,068,853 A | 5/2000 | Giannos et al. |
| 6,068,856 A | 5/2000 | Sachs et al. |
| 6,090,401 A | 7/2000 | Gowan et al. |
| 6,099,859 A | 8/2000 | Cheng et al. |
| 6,106,864 A | 8/2000 | Dolan et al. |
| 6,183,776 B1 | 2/2001 | Depui et al. |
| 6,183,777 B1 | 2/2001 | Chen et al. |
| 6,194,001 B1 | 2/2001 | Gribbon et al. |
| 6,210,710 B1 | 4/2001 | Skinner |
| 6,228,400 B1 | 5/2001 | Lee et al. |
| 6,251,432 B1 | 6/2001 | Mazer et al. |
| 6,261,582 B1 | 7/2001 | Needham et al. |
| 6,270,804 B1 | 8/2001 | Getz et al. |
| 6,296,876 B1 | 10/2001 | Odidi et al. |
| 6,312,723 B1 * | 11/2001 | Whittle ............... A61K 9/0019 424/465 |
| 6,312,724 B1 | 11/2001 | Odidi et al. |
| 6,368,635 B1 | 4/2002 | Akiyama et al. |
| 6,433,040 B1 | 8/2002 | Dellamary et al. |
| 6,479,075 B1 | 11/2002 | Odidi et al. |
| 6,489,346 B1 | 12/2002 | Phillips |
| 6,491,949 B2 | 12/2002 | Faour et al. |
| 6,509,037 B2 | 1/2003 | Odidi et al. |
| 6,527,051 B1 | 3/2003 | Reddy et al. |
| 6,555,127 B2 | 4/2003 | Steiner |
| 6,558,704 B1 | 5/2003 | Bartholomaeus et al. |
| 6,569,453 B2 | 5/2003 | Linder et al. |
| 6,599,529 B1 | 7/2003 | Skinhoj |
| 6,605,300 B1 | 8/2003 | Burnside et al. |

(56) References Cited

U.S. PATENT DOCUMENTS

| | | |
|---|---|---|
| 6,607,751 B1 | 8/2003 | Odidi et al. |
| 6,627,635 B2 | 9/2003 | Palermo et al. |
| 6,645,524 B2 | 11/2003 | Midha et al. |
| 6,645,528 B1 | 11/2003 | Straub et al. |
| 6,645,988 B2 | 11/2003 | Phillips |
| 6,652,882 B1 | 11/2003 | Odidi et al. |
| 6,673,367 B1 | 1/2004 | Goldenheim et al. |
| 6,676,966 B1 | 1/2004 | Odidi et al. |
| 6,696,088 B2 | 2/2004 | Oshlack et al. |
| 6,699,885 B2 | 3/2004 | Phillips |
| 6,780,882 B2 | 8/2004 | Phillips |
| 6,800,668 B1 | 10/2004 | Odidi et al. |
| 6,902,742 B2 | 6/2005 | Devane et al. |
| 6,911,217 B1 | 6/2005 | Gren et al. |
| 6,946,146 B2 | 9/2005 | Mulye |
| 6,991,804 B2 | 1/2006 | Helmus et al. |
| 7,090,867 B2 | 8/2006 | Odidi et al. |
| 7,135,465 B2 | 11/2006 | Abramowitz et al. |
| 7,157,103 B2 | 1/2007 | Sackler |
| 7,858,119 B1 | 12/2010 | Odidi et al. |
| 7,906,143 B1 | 3/2011 | Odidi et al. |
| 9,078,827 B2 | 7/2015 | Odidi et al. |
| 2001/0006649 A1 | 7/2001 | Chen |
| 2002/0002147 A1 | 1/2002 | Abramowitz et al. |
| 2002/0045646 A1 | 4/2002 | Phillips |
| 2002/0086885 A1 | 7/2002 | Odaka et al. |
| 2002/0110590 A1 | 8/2002 | Shaked et al. |
| 2002/0128293 A1 | 9/2002 | Rampal et al. |
| 2002/0132005 A1 | 9/2002 | Faour |
| 2002/0150535 A1 | 10/2002 | Madras et al. |
| 2003/0064099 A1 | 4/2003 | Oshlack et al. |
| 2003/0064101 A1 | 4/2003 | Mehta et al. |
| 2003/0068370 A1 | 4/2003 | Sackler |
| 2003/0068371 A1 | 4/2003 | Oshlack et al. |
| 2003/0118641 A1 | 6/2003 | Maloney et al. |
| 2003/0118669 A1 | 6/2003 | Phillips |
| 2003/0185887 A1 | 10/2003 | Chen et al. |
| 2003/0215507 A1 | 11/2003 | Sherman et al. |
| 2003/0215527 A1 | 11/2003 | Phillips |
| 2003/0220413 A1 | 11/2003 | Petereit et al. |
| 2003/0235616 A1 | 12/2003 | Sowden et al. |
| 2004/0048896 A1 | 3/2004 | Phillips |
| 2004/0058018 A1 | 3/2004 | Phillips |
| 2004/0101558 A1 | 5/2004 | Dietrich et al. |
| 2004/0131669 A1 | 7/2004 | Kerc |
| 2004/0171646 A1 | 9/2004 | Phillips |
| 2004/0198775 A1 | 10/2004 | Fraser et al. |
| 2004/0265370 A1 | 12/2004 | Odidi et al. |
| 2004/0265380 A1 | 12/2004 | Delmas et al. |
| 2005/0004171 A1 | 1/2005 | Phillips |
| 2005/0042304 A1 | 2/2005 | Phillips |
| 2005/0054682 A1 | 3/2005 | Phillips |
| 2005/0186268 A1 | 8/2005 | Hoshi et al. |
| 2005/0196436 A1 | 9/2005 | Chantranukul et al. |
| 2006/0003001 A1 | 1/2006 | Devane et al. |
| 2006/0004193 A1 | 1/2006 | Muller |
| 2006/0017336 A1 | 1/2006 | Knauff |
| 2006/0018948 A1 | 1/2006 | Guire et al. |
| 2006/0024361 A1 | 2/2006 | Odidi et al. |
| 2006/0039864 A1 | 2/2006 | Bartholomaus et al. |
| 2006/0039976 A1 | 2/2006 | Odidi et al. |
| 2006/0099246 A1 | 5/2006 | Tanner et al. |
| 2006/0153909 A1 | 7/2006 | Motoune |
| 2006/0205681 A1 | 9/2006 | Moaddeb |
| 2007/0003619 A1 | 1/2007 | Smith |
| 2007/0009589 A1 | 1/2007 | Raghupathi et al. |
| 2007/0077293 A1 | 4/2007 | Park |
| 2007/0104778 A1 | 5/2007 | Zeng et al. |
| 2007/0131357 A1 | 6/2007 | Wu |
| 2007/0166370 A1 | 7/2007 | Odidi et al. |
| 2007/0286902 A1 | 12/2007 | Xie et al. |
| 2009/0220613 A1 | 9/2009 | Odidi et al. |

FOREIGN PATENT DOCUMENTS

| | | |
|---|---|---|
| CA | 2551946 | 7/2005 |
| CN | 1634116 | 7/2005 |
| DE | 1204363 | 8/1964 |
| DE | 3531487 C2 | 8/1985 |
| DE | 3943242 A1 | 6/1990 |
| DE | 3531487 | 8/1995 |
| DE | 19635676 A1 | 3/1998 |
| EP | 0005129 B1 | 4/1981 |
| EP | 0174726 | 7/1985 |
| EP | 0157695 A2 | 9/1985 |
| EP | 0166287 | 10/1985 |
| EP | 0166287 B1 | 1/1986 |
| EP | 0174726 A1 | 3/1986 |
| EP | 0184322 | 6/1986 |
| EP | 0184322 B1 | 11/1986 |
| EP | 0234485 | 2/1987 |
| EP | 0234485 B1 | 2/1987 |
| EP | 0261478 | 4/1987 |
| EP | 0080341 | 10/1987 |
| EP | 080341 B1 | 10/1987 |
| EP | 0268956 | 11/1987 |
| EP | 0261478 A1 | 3/1988 |
| EP | 0268956 B1 | 6/1988 |
| EP | 0270305 A2 | 6/1988 |
| EP | 0342522 A1 | 11/1989 |
| EP | 0366321 A1 | 5/1990 |
| EP | 0434999 | 11/1990 |
| EP | 0403383 A1 | 12/1990 |
| EP | 0434999 B1 | 7/1991 |
| EP | 0453001 A1 | 10/1991 |
| EP | 0527638 A1 | 2/1993 |
| EP | 0533790 B1 | 3/1993 |
| EP | 0533790 | 10/1997 |
| EP | 0797991 A1 | 10/1997 |
| EP | 99/12524 | 3/1999 |
| EP | 0960620 A1 | 12/1999 |
| EP | 1017370 B1 | 7/2000 |
| EP | 2529984 | 12/2000 |
| EP | 1493435 | 1/2005 |
| FR | 2419722 A1 | 1/1979 |
| FR | 2621012 | 9/1989 |
| FR | 2778848 | 11/1999 |
| GB | 2163747 | 3/1983 |
| GB | 2134516 A | 8/1984 |
| GB | 2163747 A | 3/1986 |
| HU | 203477 B | 1/1991 |
| JP | 2002-068964 | 3/2002 |
| JP | 2005508359 | 3/2005 |
| JP | 2005515153 | 5/2005 |
| WO | WO8503436 A1 | 8/1985 |
| WO | WO8705212 A1 | 9/1987 |
| WO | WO9011070 A1 | 10/1990 |
| WO | WO9107950 A1 | 6/1991 |
| WO | WO9116885 A1 | 11/1991 |
| WO | 91/19710 | 12/1991 |
| WO | WO9119710 A1 | 12/1991 |
| WO | WO9204013 A1 | 3/1992 |
| WO | 92/08716 | 5/1992 |
| WO | WO9208716 A1 | 5/1992 |
| WO | WO9323770 A1 | 7/1993 |
| WO | WO9428882 A1 | 12/1994 |
| WO | WO9816206 A1 | 4/1998 |
| WO | WO9851287 A1 | 11/1998 |
| WO | WO99/12524 | 3/1999 |
| WO | WO9912524 A1 | 3/1999 |
| WO | WO0137817 A1 | 5/2001 |
| WO | 0230398 | 4/2002 |
| WO | 0230398 A2 | 4/2002 |
| WO | WO0230398 A2 | 4/2002 |
| WO | 03/009846 | 2/2003 |
| WO | WO03009846 A1 | 2/2003 |
| WO | 03086364 A1 | 10/2003 |
| WO | WO04000825 A1 | 12/2003 |
| WO | 2004024128 | 3/2004 |
| WO | 2004056354 A1 | 7/2004 |
| WO | WO2004056354 A1 | 7/2004 |
| WO | 2005032474 | 1/2005 |

(56) References Cited

FOREIGN PATENT DOCUMENTS

| WO | 2005021009 A2 | 3/2005 |
|---|---|---|
| WO | 2005065661 A2 | 7/2005 |
| WO | 2005097075 | 10/2005 |
| WO | 2005097075 A2 | 10/2005 |
| WO | 2006011592 | 2/2006 |
| WO | 2006017336 A2 | 2/2006 |
| WO | 2006085335 A2 | 8/2006 |

OTHER PUBLICATIONS

Drugs Made in Germany, 37 No. 2 (1994), pp. 53-60, "Fast Disintegrating Controlled Release Tablets from Coated Particles", K. Lehmann, H. U. Petereit and D. Dreher.
Banga, A. et al., "Incorporation of Simethicone into Syrup or Clear Base Liquid Orals", Drug Development and Industrial Pharmacy, (1989), vol. 15(5), pp. 671-704.
Aulton M.E. (Churchill Livingstone Ed.), Pharmaceutics: The science of dosage form design (1988), p. 316-321.
Dashevsky, A. et al., pH-independent Release of Basic Drug from Pellets Coated with the Extended Release Polymer Dispersion Kollicoat SR 30 D and the Enteric Polymer Dispersion Kollicoat MAE 30 DP, European Journal of Pharmaceutics and Biopharmaceuticals, (2004), vol. 58, pp. 45-49 (available online Jun. 1, 2004).
Deshpande, A. et al., Development of a Novel Controlled-Release System for Gastric Retention, Pharmaceutical Research, (1997) vol. 14, No. 6, pp. 815-819.
Krogel, I. et al., Floating of Pulsatile Drug Delivery Systems Based on Coated Efferescent Cores, International Journal of Pharmaceutics, (19990 vol. 187, pp. 175-184 anl.
Laizure, S. C. et al., Stability of Bupropion and its Major Metabolites in Human Plasma, Therapeutic Drug Monitoring (1985), vol. 7(4): p. 447.
Lehmann, K. et al.,—Fast Disintegrating Controlled Release Tablets from Coated Particles—Drug Made in Germany, (1994) vol. 37, No. 2, pp. 53-60.
Martindale, The Extra Pharmacopoeia, 30th Ed. (The Pharmaceutical Press, London 1993).
European Patent Application No. 04 737 769.2-2112, Examination Report dated Nov. 18, 2009.
International Search Report and Written Opinion mailed Oct. 22, 2004 for PCT Application PCT/CA2004/000825 filed Jun. 3, 2004.
Conner et al. A scintigraphic study to investigate the potential for altered gut distribution of loperaminde from a loperaminde-simethicone formation in man, European Journal of Pharmaceutical Sciences, 13 (2001) p. 369-374.
Sungthongjeen et al Development of pulsatile release tablets with swelling and rupturable layers, Journal of Controlled Release, 95 (2004) p. 147-159.
Canadian Intellectual Property Office, Office Action dated Nov. 15, 2013 in CA application 2,579,382, 2 pages.
Canadian Intellectual Property Office, Office Action dated Dec. 4, 2013 in CA application 2,648,278, 3 pages.
European Patent Office, Examination Report of Sep. 24, 2013 for EP application 07 719 478.5-1455, 6 pages.
Super Disintegrates: Characterizations and Function (From European Examination Report of #3 above), 2007 by Informa Healthcare USA, Inc., 18 pages.
Office Action dated Sep. 28, 2009 for U.S. Appl. No. 10/861,809.
Office Action dated Nov. 26, 2008 for U.S. Appl. No. 10/861,809.
Office Action dated Nov. 13, 2007 for U.S. Appl. No. 10/861,809.
Merriam-Webster Dictionary; definition of "Paste"; 1 page, accessed Dec. 16, 2014.

* cited by examiner

PROTON PUMP-INHIBITOR-CONTAINING CAPSULES WHICH COMPRISE SUBUNITS DIFFERENTLY STRUCTURED FOR A DELAYED RELEASE OF THE ACTIVE INGREDIENT

CROSS-REFERENCE TO RELATED APPLICATIONS

This application claims priority to and is a divisional of U.S. Non-Provisional application entitled, "PROTON PUMP-INHIBITOR-CONTAINING CAPSULES WHICH COMPRISE SUBUNITS DIFFERENTLY STRUCTURED FOR A DELAYED RELEASE OF THE ACTIVE INGREDIENT", having Ser. No. 10/751,700, filed on Nov. 10, 2006, now issued as U.S. Pat. No. 8,802,139, which is the 35 U.S.C. §371 national stage of, and claims priority to and the benefit of, PCT application PCT/CA04/00825, filed Jun. 3, 2004, which claims priority to and the benefit of U.S. Provisional Application No. 60/548,903, filed Mar. 2, 2004 and which claims priority to and the benefit of U.S. Provisional Application No. 60/482,439, filed Jun. 26, 2003, which are all incorporated herein by reference in thier entirety.

FIELD OF THE INVENTION

The present invention relates to oral pharmaceutical preparations and methods of making such preparations. More specifically, the invention is a multi-functional pharmaceutical capsule (MFC) that comprises multiple populations of pharmaceutical actives together with multiple populations of a basic substance either of which is provided as beads, pellets, tablets and/or granules. Each population is functionally distinct. The capsule provides multiple site specific delivery of a pharmaceutical active in a rapid, delayed and/or sustained release manner into the plasma.

BACKGROUND OF THE INVENTION

Throughout this application, various references are cited to describe more fully the state of the art to which this invention pertains. The disclosure of these references are hereby incorporated by reference into the present disclosure.

Acid labile $H^+K^+$-ATPase inhibitors, known as gastric proton pump inhibitors (PPI), are known and include the generic compounds such as omeprazole, lansoprazole, pantoprazole, pariprazole, rabeprazole and leminoprazole as disclosed for example in U.S. Pat. Nos. 4,045,563; 4,255,431; 4,628,098; 4,686,230; 4,758,579; 4,965,269; 5,021,433; 5,430,042 5,045,552 and 5,708,017. In general, the proton pump inhibitors of gastric acid secretion work by undergoing a rearrangement to form a thiophilic species which then covalently binds to gastric $H^+K^+$ATPase, the enzyme involved in the final step of proton production in the parietal cells, and thereby inhibits the enzyme.

Proton pump inhibitor compounds are useful for inhibiting gastric acid secretion in mammals and man and are used for prevention and treatment of gastric acid related diseases such as reflux esophagitis, gastritis, duodenitis, gastric ulcer and duodenal ulcer. Furthermore, they may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. They may also be used in patients in intensive care situations, in patients with acute upper gastrointestinal bleeding, pre- and postoperatively to prevent acid aspiration of gastric add and to prevent and treat stress ulceration. Further, they may be useful in the treatment of psoriasis as well as in the treatment of *Helicobacter* infections and diseases related to these.

Proton pump inhibitor compounds are susceptible to degradation or transformation in acidic media. The degradation is catalyzed by acidic compounds and is more stabilized in mixtures with alkaline compounds. The stability of proton pump inhibitor compounds may also be affected by moisture, heat, organic solvents and to some degree by light. For example, proton pump inhibitor compounds such as pyridyl methyl sulfinyl benzimidazoles (having a $pK_a$ of 4.0 to 5.0) have a mechanism of action requiring accumulation in the acidic space of the parietal cell (secretory canaliculus, pH ca. 1.0) followed by subsequent hydrogen ion catalyzed conversion to the reactive thiophilic species that is capable of inhibiting the gastric ATPase enzyme resulting in effective inhibition of gastric secretion. Due to this mechanism this compound requires specialized gastro protection to remain active for duodenal absorption. For this reason, and due to sensitivity to degradation in the acid milieu of the stomach, oral formulations of proton pump inhibitor compounds are usually enteric coated. The need for enteric coating is a shortcoming because enteric coatings are expensive to provide and pH sensitive. Furthermore, the use of enteric coating means that the compound is not being released for absorption in the stomach. Enteric coating layers are known and disclosed for example in U.S. Pat. Nos. 4,853,230, 6,479,075 and 6,296,876.

U.S. Pat. No. 5,753,265 discloses an enteric coating layered multiple unit tablet that disperses into a multitude of small units in the stomach upon administration. Many different types of multiple unit dosage forms are known in the prior art. Usually this type of formulation is requested for controlled release formulations, such as sustained release formulations. Typically, the multiple unit formulation may be a tablet which disintegrates in the stomach to make available a multitude of coated units, or pellets filled in a capsule as is disclosed in EP 0 080 341 and U.S. Pat. No. 4,853,230. However, these do not allow for delivery of the proton pump inhibitor compound throughout the gastrointestinal tract (GIT).

U.S. Pat. No. 4,927,640 discloses a controlled release dosage form that releases the active substance by diffusion through a membrane. The dosage form is a multiple-unit system containing small inert cores coated with active substance and a release controlling polymeric membrane. Other examples of controlled release dosage forms are, for example, described in Aulton M. E. (Churchill Livingstone Ed.), Pharmaceutics: The science of dosage form design (1988), p. 316-321. These dosage forms do not sufficiently address the stability issues of the proton pump inhibitor compounds during transit in the gastrointestinal tract.

In practice, problems also arise when enteric coating layered pellets containing acid labile substances, such as proton pump inhibitor compounds, are compressed into tablets. If the enteric coating layer does not withstand the compression of the pellets into a tablet, the susceptible active substance will be destroyed by penetrating acidic gastric juice, i.e. the acid resistance of the enteric coating layer of the pellets will not be sufficient in the tablet after compression. Further, controlled release tablets from enteric coated particles are described in the article: Drugs Made In Germany, 37 No. 2 (1994), p. 53. This reference teaches a combination of methacrylic acid copolymer (L30D-55) and a copolymer of ethyl acrylate and methyl methacrylate (NE30D) suitable as a coating polymer for enteric coated particles compressed into tablets. However, the acid resistance of the pellets compressed into tablets is low.

U.S. Pat. No. 6,183,776 discloses an oral pharmaceutical dosage form comprising an acid susceptible proton pump inhibitor together with an antacid agent or an alginate in a fixed formulation, wherein the proton pump inhibitor is protected by an enteric coating layer and an optional separating layer is present between the proton pump inhibitor and the enteric coating. The fixed formulation is in the form of a multi-layered tablet, sachets or multiple unit tableted dosage form.

The prior art also describes fixed formulations in the form of multiple unit tablets with alkalinizing agents. These multiple unit dosage forms are not the most preferred because the enteric coated proton pump inhibitor is dumped only in the stomach due to the presence of the alkalinizing agent, where the drug is rapidly absorbed and has a short half life.

Acid secretion is necessary for the efficacy of proton pump inhibitor compounds because of the requirement for accumulation in the acid space of the parietal cell. Typical plasma half life of proton pump inhibitor compounds and formulations is only between 60 to 90 minutes. As not all acid pumps are active at any one time, rather only about 75% are active on the average during the time the drug is present in the blood following oral administration, in a currently used once-a-day oral administration therapy the maximum inhibition of stimulated acid output is approximately 66%. This is due to a combination of the short plasma half-life of the proton pump inhibitor compound, to the limited number of acid pumps active during presentation of the compound, and to the turn over of acid pumps. Furthermore, in current therapies it is not possible to control night-time acid secretion by an evening therapy of oral administration because the compound is dissipated from the plasma by the time acid secretion is established after midnight.

The ideal target for healing in acid related diseases and for treatment of *H. pylori* infection (in conjunction with antibiotics), as well as for relief of symptoms of non-ulcer dyspepsia, would be full inhibition of acid secretion. With the currently used proton pump inhibitor formulations, this is achieved only by intravenous infusion. In the case of the drug omeprazole, intravenous infusion of 8 mg per hour is required.

Clearly, there is a need in the art for a formulation of a proton type inhibitor compound, which can attain or approach full inhibition of acid secretion through oral therapy. There is a demand for the development of a novel proton pump inhibitor formulation that provides good chemical stability and more precise control of the release of the proton pump inhibitor compound within the gastrointestinal environment.

SUMMARY OF THE INVENTION

According to an aspect of the present invention, there is provided an oral pharmaceutical composition comprising multiple populations of at least one of beads, pellets, tablets and granules provided in a capsule, the composition comprising:

(i) a first population of a pharmaceutical active comprising a pharmaceutical active substance releasable at a first rate;

(ii) a population of a basic substance; and (iii) a second population of a pharmaceutical active comprising a pharmaceutical active substance releasable at a second rate.

According to another aspect of the present invention, there is provided an oral pharmaceutical composition comprising multiple populations at least one of beads, pellets, tablets and granules provided in a capsule, the composition comprising:

(i) a population of a pharmaceutical active;

(ii) a population of a basic substance;

(iii) a population of enteric coated pharmaceutical active; and (iv) a population of enteric coated basic substance.

In certain aspects of the invention, the population of either (i) to (iv) is formed about a core material, for example, a sugar sphere or microcrystalline cellulose of about 0.1 mm to about 4 mm. Alternatively, the population of either (i) to (iv) is provided as a tablet of about 0.5 mm to about 20 mm. All populations are then provided within a suitable capsule material for oral administration by various mechanisms as further described herein.

In further aspects of the invention, the population of either (i) to (iv) may be about 0.1 mm to about 25 mm and any desired size therebetween.

According to another aspect of the present invention, there is provided an oral pharmaceutical composition comprising multiple populations of at least one of beads, pellets, tablets and granules provided in a capsule, the composition comprising:

(i) a population of a proton pump inhibitor compound;

(ii) a population of a basic substance;

(iii) a population of enteric coated proton pump inhibitor compound; and (iv) a population of enteric coated basic substance, wherein a separating layer is provided in one or both of (iii) or (iv) to separate the proton pump inhibitor compound or the basic substance from the enteric coating.

In aspects, one or more of the populations of (i) to (iv) may further be provided with one or more over-coating layers.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

DETAILED DESCRIPTION OF THE INVENTION

The present invention is a multi-functional pharmaceutical capsule for oral use that comprises multiple populations in the form of pellets, tablets, beads and/or granules of a pharmaceutical active substance and multiple populations in the form of pellets, tablets, beads and/or granules of a basic substance, either of which may be optionally coated with a separating layer. A portion of the pharmaceutical active substance and basic substance populations may also be further enteric coated. All of the populations are then provided within a capsule for oral administration to a subject in need of such treatment.

The capsule is suitable for direct oral administration or alternatively may be provided dispersed within a suitable liquid for administration to a subject with swallowing disorders or formulated for pediatric administration. For example, the capsule may be dispersed within apple sauce or alternatively, in a suitable liquid for feeding through a naso-gastric tube.

In embodiments of the invention, a pharmaceutical multi-functional oral dosage capsule comprising multiple populations of pharmaceutical actives are designed to release the pharmaceutical active substance in a rapid, delayed, and/or sustained manner in the gastrointestinal tract (GIT). For instance, the active substance can be delivered to the stomach, between the duodenum and just past the ileocecal junction, and/or further to the ascending, transverse and descending colon. This is also effected through the use of the enteric coated and/or non-enteric coated basic substance. The populations of pharmaceutical actives may be optionally enteric coated. The term "sustained" release is understood to encompass controlled release, extended release, slow release and/or the like.

The capsule of the invention can provide for the control of night time acid secretion in a subject with an evening therapy of oral administration. Multiple peaks of the pharmaceutical active substance (e.g. proton pump inhibitor) plasma concentrations may be obtained between one to three, four, six, eight, twelve, sixteen or twenty four hours.

In one embodiment, the multi-functional pharmaceutical capsule comprises a population of the pharmaceutical active, which is designed to release the active substance at a first rate, for instance in a rapid manner, such that the active substance can be delivered to the stomach. A further population of the pharmaceutical active, which is designed to release the active substance at a second rate, for instance in a delayed or sustained manner, such that the active substance can be delivered between the duodenum and just past the ileocecal junction and/or further to the ascending, transverse and descending colon. This is also effected through the use of the enteric coated and/or non-enteric coated basic substance.

In another embodiment, the multi-functional pharmaceutical capsule comprises a non-enteric coated population of the pharmaceutical active, wherein the pharmaceutical active is delivered to the stomach. A further enteric coated population of pharmaceutical active is delivered between the duodenum and just past the ileocecal junction and a further enteric coated population of the pharmaceutical active is delivered to the ascending, transverse and descending colon. This is also effected through the use of the enteric coated and/or non-enteric coated basic substance.

As such, the pharmaceutical active substance (e.g. proton pump inhibitor) according to the invention is delivered to multiple sites in the gastrointestinal tract beginning with the stomach despite its acidic environment.

In a more specific embodiment of the invention, the multi-functional pharmaceutical capsule comprises:

a first population of pharmaceutical active provided as beads, pellets, tablets or granules and combinations thereof, wherein the pharmaceutical active comprises a pharmaceutical active substance that is rapidly releasable;

a second population of pharmaceutical active provided as beads, pellets, tablets or granules and combinations thereof, wherein the pharmaceutical active comprises an excipient and a pharmaceutical active substance that is released slower than that of the first population; and a population of basic substance provided as beads, pellets, tablets or granules and combinations thereof.

The pharmaceutical capsule of the invention is made such that each population of beads, pellets, tablets or granules has a distinct physiological function.

The function of the first population, comprising the pharmaceutically active substance, such as a proton pump inhibitor compound (PPI), that is rapidly releasable, is to deliver the pharmaceutical active beginning in the stomach. This is made possible due to the presence of an optional excipient and by the stable environment created by the elevated pH environment of the stomach brought about by the rapid disintegration and dissolution of the population of basic substance whose function is to rapidly deliver basic material to the stomach, which allows for precise control of the stomach pH to more than about 4.0 and less than about 7.0 and, typically, less than about pH 6.3. This pH can also be achieved in less than about 1 hour.

The function of the second population, comprising the pharmaceutical active substance, such as a proton pump inhibitor compound (PPI), that is released slower than that of the first population, is to deliver another quantity of the pharmaceutical active between the duodenum and just past the ileocecal junction. This is possible due to the presence of an excipient that controls the release of the pharmaceutical active and the choice and quantity of the basic substance delivered in the stomach by the population of basic substance. The pharmaceutical active substance of the second population may be released in a delayed and/or sustained manner.

The population of either or both the pharmaceutical active substance and the basic substance can be formulated with suitable excipients as is understood by one of skill in the art, keeping in mind the desired rates of releasability of the pharmaceutical active. For example, the excipient, if any, chosen for the first population of the pharmaceutical active will allow for the rapid releasability of the pharmaceutical active. The excipient chosen for the second population of the pharmaceutical active will allow for a comparably less rapid releasability of the pharmaceutical active. Specifically, the excipient for the first population of the pharmaceutical active may be a disintegrating agent and the excipient for the second population of the pharmaceutical active may be a sustained release agent.

In further embodiments, the population(s) of pharmaceutical active(s) have enteric coating(s). The population(s) of pharmaceutical active(s) that have enteric coating(s) can be optionally formulated to have a separating layer prior to the provision of an enteric coating. The separating layer separates the pharmaceutical active from the enteric coating to prevent any reaction occurring between the pharmaceutical active and the enteric coating. Use of the enteric coating can provide the release of the pharmaceutical active in a delayed manner.

In certain aspects of the invention, the pharmaceutically active substance is an acid labile drug and typically, the pharmaceutically active substance is a proton pump inhibitor compound.

The pharmaceutical capsule of the invention may further comprise another population of a basic substance, wherein the basic substance is released less rapidly compared to the original basic substance. The use of an excipient and/or the use of an enteric coating may control the release of the basic substance. A separating layer may also be provided, for similar reasons given above, prior to the addition of the enteric coating.

Additional populations of pharmaceutical actives may be added to expand on the variability of release of the pharmaceutical active substance. For example, multiple populations of the pharmaceutical active with varying release rates can establish a pulsed release capsule. For instance, a rapid release population, a delayed release population and a sustained release population of pharmaceutical actives together with multiple populations of a basic substance provide one type of pulsed release capsule.

In another specific embodiment of the invention, the multi-functional pharmaceutical capsule comprises:

a population of pharmaceutical active substance provided as beads, pellets, tablets or granules and combinations thereof;

a population of pharmaceutical active substance provided as beads, pellets, tablets or granules and combinations thereof having an enteric coating thereon;

a population of basic substance provided as beads, pellets, tablets or granules and combinations thereof; and a population of basic substance provided as beads, pellets, tablets or granules and combinations thereof having an enteric coating thereon.

An optional separating layer is provided to the populations of pharmaceutical active and basic substance having an enteric coating thereon, the separating layer being provided between the pharmaceutical active or basic substance and the enteric coating layer(s).

The population of either or both the pharmaceutical active substance and the basic substance can be formulated with suitable excipients as is understood by one of skill in the art. Furthermore, the population of pharmaceutical active substance can be optionally formulated to have a separating layer prior to the provision of an enteric coating. Such a separating layer may also be incorporated into a population of the basic substance. In certain aspects of the invention, the pharmaceutically active substance is an acid labile drug and, typically, the pharmaceutically active substance is a proton pump inhibitor compound.

The function of the population containing pharmaceutically active substance being a proton pump inhibitor compound (PPI) is to deliver the pharmaceutical active beginning in the stomach. This is made possible by the stable environment created by the elevated pH environment of the stomach brought about by the rapid disintegration and dissolution of the population of basic material whose function is to rapidly deliver basic material to the stomach.

The function of the population containing pharmaceutical active substance being a proton pump inhibitor compound (PPI) having an enteric coating thereon is to deliver another quantity of the pharmaceutical active between the duodenum and just past the ileocecal junction. This is possible due to the presence of the enteric coat and the choice and quantity of the basic material delivered in the stomach by the population of basic material, which allows for precise control of the stomach pH to more than about 4.0 and less than about 7.0 or, typically, less than about pH 6.3. This pH can also be achieved in less than about 1 hour.

The function of the population containing basic material having an enteric coating thereon is to deliver a second quantity of basic material to just past the ileocecal junction to help maintain the pH of the colon to a value not less than about pH 5.0, as a result of which any residual active substance will not be degraded by acid environment that may be encountered in the colon. It is not uncommon for the pH of some sections of the colon to fall to an acidic level.

The invention is suitable for acid labile drugs in general. In embodiments, the acid labile drug is a proton pump inhibitor, a prodrug of a proton pump inhibitor, enantiomers thereof and/or combinations thereof. Suitable proton pump inhibitor pharmaceutical actives for use in the present invention are compounds of gastric proton pump inhibitors or an alkaline salt thereof or one of its single enantiomers or an alkaline salt thereof. The compounds may be used in neutral form or in the form of an alkaline salt, such as for instance the $Mg^{2+}$, $Ca^{2+}$, $Na^+$ or $K^+$ salts, and more typically $Mg^{2+}$ salts.

Examples of acid-labile proton pump inhibitors ($H^+/K^+$ ATPase inhibitors) for use in the present invention are substituted pyridin-2-ylmethylsulfinyl-1H-benzimidazoles, such as are disclosed, for example, in EP-A-0 005 129, EP-A-0 166 287, EP-A-0 174 726, EP-A-0 184 322, EP-A-0 261 478 and EP-A-0 268 956. In typical embodiments, the inhibitors are 5-methoxy-2-[(4-methoxy-3,5-dimethyl-2-pyridinyl)methylsulfinyl]-1H-benzi-midazole (INN: omeprazole), 5-difluoromethoxy-2-[(3,4-dimethoxy-2-pyridinyl)methylsulfinyl]-1H-benzim-idazole (INN: pantoprazole), 2-[3-methyl-4-(2,2,2-trifluoroethoxy)-2-pyridinyl)methyl-sulfinyl]-1H-ben-zimidazole (INN: lansoprazole) and 2-{[4-(3-methoxypropoxy)-3-methylpyridin-2-yl]methyl-sulfinyl}-1H-benzimidazole (INN: rabeprazole).

Still other suitable acid-labile proton pump inhibitors are for example substituted phenylmethylsulfinyl-1H-benzimidazoles, cycloheptapyridin-9-ylsulfinyl-1H-benzimidazoles or pyridin-2-ylmethylsulfinylthienoimidazoles as disclosed in DE-A-35 31 487, EP-A-0 434 999 or EP-A-0 234 485. In embodiments are 2-[2-(N-isobutyl-N-methylamino)benzyl-sulfinyl]benzimidazole (INN: leminoprazole) and 2-(4-methoxy-6,7,8,9-tetrahydro-5H-cyclohepta[b]pyridin-9-yl-sulfinyl)-1H-benzimidazole (INN: nepaprazole).

Acid-labile proton pump inhibitors are chiral compounds. As such, an "acid-labile proton pump inhibitor" also includes the pure enantiomers of the acid-labile proton pump inhibitors and their mixtures in any mixing ratio including the racemates. Enantiomerically pure acid-labile proton pump inhibitors are disclosed, for example, in WO92/08716 and may include for example Esomeprazole.

The acid-labile proton pump inhibitors are present here as such or are typically in the form of their salts with bases. Examples of salts with bases which may be mentioned are sodium, potassium, magnesium or calcium salts. If desired, the salts of the acid-labile proton pump inhibitors with bases can also be present in hydrate form. Such a hydrate of the salt of an acid-labile proton pump inhibitor with a base is disclosed, for example, in WO 91/19710.

The pharmaceutical active substance for use in one or more populations of the capsule of the invention may include up to about 80% by weight of the pharmaceutical active in the bead, pellet, tablet or granule. It is understood by one of skill in the art that for human oral delivery, a high drug content is desirable in order that the capsule not be too large for comfortable human oral administration. For veterinary applications, less active can be incorporated per bead, pellet, tablet or granule as the size of the final capsule can be much larger as compared for human oral administration. In embodiments, the amount of proton pump inhibitor active may comprise about 0.1 mg to about 5000 mg in the capsule.

It is understood by one of skill in the art that one or a combination of proton pump inhibitor compounds as described herein may be used within a single capsule formulation. It is also understood by one of skill in the art, that in addition to the proton pump inhibitor compounds, additional drugs such as, but not limited to, non-steroidal anti-inflammatory agents, prokinetic agents, anticancer agents, anti-emetic agents and combinations thereof may be incorporated into the present capsule formulation and be presented as a population of beads, pellets, tablets and/or granules that may be further enteric coated and may be further provided with a separating layer as described herein. As such, the present invention is suitable for the treatment of a variety of disorders including but not limited to inappropriate gastric acid secretion, reflux esophagitis, gastritis, duodenitis, gastric ulcer, duodenal ulcer, non-ulcer dyspepsia, symptomatic gastro-esophageal reflux disease, gastrinoma, acute upper gastrointestinal bleeding, stress ulceration, psoriasis, *helicobacter* disorders and gastrointestinal disorders caused by the use of non-steroidal anti-inflammatory drugs (NSAIDs).

Suitable substances for use as the basic material of the invention may be selected from, but not restricted to, substances such as the sodium, potassium, calcium, magnesium and aluminium salts of phosphoric acid, carbonic acid, citric acid or other suitable weak inorganic or organic acids; aluminium hydroxide/sodium bicarbonate co-precipitate; substances normally used in antacid preparations such as aluminium, calcium and magnesium hydroxides; magnesium oxide or composite substances, such as $Al_2O_3 6MOCO_2 12H_2O$, $Mg_6Al_2(OH)_{16}CO_3 4H_2O$, $MgOAl_2O_3 2(SiO_2)_n H_2O$ or similar compounds, organic pH-buffering substances such as trihydroxymethylaminomethane, basic amino acids and their salts or other similar, pharmaceutically acceptable pH-buffering substances. The choice and quantity of the basic material is optimized for effective pH control. It is also understood by one of skill in the art that a combination of one or more different basic materials may be used in a population of basic material.

The basic substance for use in one or more populations of the capsule of the invention may include up to about 80% by weight of basic substance of the bead, pellet, tablet or granule. In formulations of the capsule of the invention the amount of basic substance may be about 0.1 mg to about 5000 mg. In aspects of the invention the basic substance is capable of raising the pH of a 290 ml of HCl solution of pH 2.2 to between pH 4.0 to pH 7.5 in about 15 minutes and not less than about pH 5.5 or more than pH 7.5 for about 48 hours.

To the pharmaceutical active substance or basic material may be added suitable excipients as is understood by one of skill in the art. Excipients are used to obtain preferred handling and processing properties and suitable concentrations of the pharmaceutical active substance. Suitable excipients may be selected from binders, surfactants, fillers, lubricants, disintegrating agents, sustained release agents or other pharmaceutically acceptable ingredients, and combinations thereof. Binders may be selected from, for example, a variety of cellulose derivatives such as hydroxypropyl methylcellulose, hydroxypropyl cellulose and carboxymethyl-cellulose sodium, polyvinyl pyrrolidone, sugars, starches, carrageenan and other pharmaceutically acceptable substances with cohesive properties. Suitable surfactants are found in the groups of pharmaceutically acceptable non-ionic or ionic surfactants such as for instance sodium lauryl sulfate. Some examples of sustained release agents, which may in some cases function as a binder, are pectin, polyvinyl alcohol, polyvinyl acetate, hydroxypropyl cellulose, methylcellulose, ethylcellulose, hydroxypropyl methylcellulose, carrageenan, xanthan gum, carbomer, and the like and mixtures thereof. Some examples of disintegrating agents are Crospovidone™ (ie. homopolymer cross-linked N-vinyl-2-pyrrolidone), sodium starch glycolate, Croscarmelose™ (ie. cross-linked sodium carboxymethylcellulose), and the like and mixtures thereof.

The amount of excipient per bead, pellet, tablet or granule may comprise about 0.5% to about 95% wgt/wgt of a population in which it is used.

One or more optional separating layers comprising pharmaceutical excipients can be provided to a population of pharmaceutical active substance or basic substance prior to the provision of an enteric coating. The separating layer separates the pharmaceutical active from the outer enteric coating layer.

The separating layer(s) can be applied by coating or layering procedures in suitable equipment such as coating pan, coating granulator or in a fluidized bed apparatus using water and/or organic solvents for the coating process. As an alternative the separating layer(s) can be applied to the pharmaceutical active or basic substance (provided on a core material discussed further herein) by using powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carrageenan, microcrystalline cellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives may also be included into the separating layer(s).

When the optional separating layer(s) is applied to the core material it may constitute a variable thickness. The maximum thickness of the optional separating layer(s) is normally only limited by processing conditions. Generally, about 0.25% to about 50% by weight of the total bead, pellet, tablet or granule may be provided.

One or more enteric coating layers may be applied to a population of pharmaceutical active substance or to a population of basic material either of which may be optionally covered with separating layer(s) as described herein using a suitable coating technique as is understood by one of skill in the art. The enteric coating material may be dispersed or dissolved in either water or in suitable organic solvents. As enteric coating polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac, zein or other suitable enteric coating polymer(s).

The enteric coating layers contain pharmaceutically acceptable plasticizers to obtain the desired mechanical properties, such as flexibility and hardness of the enteric coating layers. Such plasticizers are for instance, but not restricted to, triacetin, citric acid esters, phthalic acid esters, dibutyl sebacate, cetyl alcohol, polyethylene glycols, polysorbates or other plasticizers. The amount of plasticizer is optimized for each enteric coating layer formula, in relation to selected enteric coating layer polymer(s), selected plasticizer(s) and the applied amount of said polymer(s), in such a way that the release properties are adjusted so that the acid resistance of the pellets covered with enteric coating, layer(s) is optimal. The amount of plasticizer is usually above about 10% by weight of the enteric coating layer polymer(s), about 15-50%, or about 20-50%. Additives such as dispersants, colorants, pigments, polymers e.g. poly(ethyl acrylat), poly(methyl methacrylate), anti-tacking and anti-foaming agents may also be included into the enteric coating layer(s). Other compounds may be added to increase film thickness and to decrease diffusion of acidic gastric juices into the enteric coated populations.

To protect the second population of active substance or basic material and to obtain an acceptable acid resistance the enteric coating layer(s) constitutes a polymer weight gain of approximately 0.5% to 85% wgt/wgt of the population, or approximately 2% to 15% weight gain. The maximum weight of the polymer in the applied enteric coating layer(s) is normally only limited by processing conditions.

Populations of pharmaceutical active or populations of basic substance each of which has an enteric coating layer(s) and optional separating layers may further be covered with one or more over-coating layer(s). The over-coating layer(s) can be applied by coating or layering procedures using suitable equipment such as a coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, carrageenan, microcrystalline cellulose, hydroxypropyl methyl cellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives may also be included into the over-coating layer(s). Said over-coating layer may further prevent potential agglomeration of enteric coating layered pellets or tablets. The maximum thickness of the applied over-coating layer(s) is normally only limited by processing conditions. In general, the amount of over-coating layer is about 0.25% to about 90% weight gain as a percent of weight of a population of bead, pellet, tablet or granule to be coated can be provided.

The population of pharmaceutical active substance can be made by layering the pharmaceutical active on sugar or cellulose spheres (herein referred to as a core material), by extrusion spheronization or by mixing the pharmaceutical active substance with a selected excipient and compressing the mixture into tablets. An enteric coating is then provided to a portion of the population of the pharmaceutical active substance. The population containing the basic substance can also be made by layering the basic substance on sugar or cellulose spheres (core material) or by extrusion spheronization or by mixing the basic substance with tablet excipients and compressing the mixture into tablets. An enteric coating is then provided to a portion of the population of the basic substance as desired.

The enteric coated populations of pharmaceutically active substance and populations of basic material should demonstrate a measure of acid resistance defined as the amount of active substance or basic material in tablets or pellets after being exposed to simulated gastric fluid, USP, or to 0.1 M HCl(aq) relative to that of unexposed tablets or pellets, respectively. The test is carried out in the following manner. The enteric coated beads, tablets or pellets are exposed to phosphate buffer pH 1.5 at a temperature of 37° C. in a USP dissolution apparatus for 2 hours. The tablets should not disintegrate and release more than about 10% of the active or basic material. After two hours the enteric coating layered beads, pellets tablets or granules are exposed to phosphate buffer (pH 7.2) and not less than about 70% of the active of basic material is released in one hour following such exposure.

The size of the sugar or cellulose spheres as a core material is not essential for the present invention but may vary between about 0.1 and about 4 mm. The spheres layered with pharmaceutical active substance or basic material are produced either by powder or solution/suspension layering using for instance granulating or spray coating/layering equipment. Alternatively a population of pellets may be produced by extrusion/spheronization, balling or compression utilizing different process equipment as is understood by one of skill in the art. The size of the formulated core materials is approximately between about 0.1 mm and 4 mm and typically, between about 0.1 mm and 2 mm. The manufactured core materials are then layered with the pharmaceutical active substance or the basic substance. Thus the size of the prepared beads, pellets, tablets or granules may vary between about 0.1 to about 25 mm and any size as desired therebetween. The tablets of the invention are made mixing the active substance or basic material with tableting excipients and compressed into a tablet to be included in the multi-functional capsule according to the present invention.

The various populations of proton pump inhibitor and basic material is provided within a suitable capsule material as is understood by one of skill in the art. Suitable capsule materials may include for example but are not limited to gelatin, cellulose ethers, cellulose, biodegradable non-toxic materials and combinations thereof. One of skill in the art would readily understand the process and manner of providing the oral composition of the invention within a capsule.

The preparation according to the invention is especially advantageous in reducing gastric acid secretion. Such a multi-functional capsule dosage form may be administered one to several times a day depending on the formulation provided within a capsule. The typical daily dose of the pharmaceutical active substance may vary and will depend on various factors such as the individual requirements of the patients, the mode of administration and the disease. In general the daily dose will be in the range of 1-400 mg of proton pump inhibitor or one of its single enantiomers or alkaline salts thereof. The preparation according to the present invention is also suitable for dispersion in an aqueous liquid with neutral or slightly acidic pH-value before being orally administered or fed through a naso-gastric tube.

Throughout the specification, it is understood that the term "a" or "an" may be interpreted to mean one or more.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

1. Preparation of Pharmaceutical Active Loaded Core Material by Extrusion Spheronization This may be used without enteric coat as first population of pharmaceutical active substances

|  | Formulation 1 (%) wgt | Formulation 2 (%) wgt | Formulation 3 (%) wgt |
|---|---|---|---|
| PPI (proton pump inhibitor) | 40 | 30 | 30 |
| Lactose | 20 | 40 | 10 |
| Starch | — | 2 | 10 |

-continued

|  | Formulation 1 (%) wgt | Formulation 2 (%) wgt | Formulation 3 (%) wgt |
|---|---|---|---|
| *Hydroxypropyl methyl cellulose | 20 | — | — |
| **Sodium lauryl sulfate | — | — | — |
| Microcrystalline cellulose | 30 | 24 | 50 |
| Eudragit ™ NE 30 D | — | 4 | — |
| ***Purified water | QS | QS | QS |

*May be replaced or combined with Xanthan gum
**Sodium lauryl sulfate is optional
***Between 10% to 100% of the total weight of excipients used is sufficient
QS—quantity sufficient

2. Preparation of Basic Material Loaded Core Material by Extrusion Spheronization This may be used without enteric coat as a population of basic material

|  | Formulation 1 (%) wgt | Formulation 2 (%) wgt | Formulation 3 (%) wgt |
|---|---|---|---|
| Basic (calcium carbonate) | 40 | 30 | 30 |
| Lactose | 20 | 40 | 10 |
| Starch 1500 | — | 2 | 10 |
| Hydroxypropyl methyl cellulose | 5 | — | — |
| Sodium lauryl sulfate | 1 | 2 | 1 |
| Microcrystalline cellulose | 45 | 26 | 49 |
| *Purified water | QS | QS | QS |

*Between 10% to 100% of the total weight of excipients used is sufficient

3. Preparation of the Optional Separation Layer for Populations of Pharmaceutical Active or Basic Material Loaded Spheres (Core Materials) to be Enteric Coated

|  | Formulation 1 (%) wgt |
|---|---|
| *Lustreclear ™ | 9 |
| Purified water | 91 |

*Carrageenan preparation. Use 3% weight gain level

4. Preparation of the Enteric Coating Layer for Population of the Pharmaceutical Active or Basic Material Loaded Spheres (Core Materials) Optionally Provided with Separating Layer

|  | *Formulation (g) |
|---|---|
| Methacrylic acid copolymer | 140 |
| PEG 600 | 28 |
| Talc | 42 |
| Purified water | 500 |

*for coating 600 g of active loaded spheres optionally covered with separating layer or 600 g of spheres loaded with basic material Sodium lauryl sulfate was dissolved in purified water and used as the granulation liquid. The PPI or basic material was dry mixed with excipients and then granulated with the aid of granulation liquid. The resultant wet mass was forced through an extruder equipped with screens with an aperture size of about 1.0 mm. The extrudate was spheronized on a friction plate in a spheronizing apparatus to form a core material which was then dried in a fluid bed dryer and classified if required.

Alternatively PPI loaded spheres were prepared by suspension layering in a fluid bed apparatus using a bottom spray technique as known to one of skill in the art. In this manner, the active was sprayed onto cellulose or sugar sphere from a water or alcohol/water suspension containing carrageenan or other suitable binder. The size of the spheres made was about 0.25 mm to about 2.0 mm.

The prepared core material was optionally covered with separating layer in a fluid bed apparatus with a Carrageenan/water solution. This is a population of pharmaceutical active substance or basic material.

To prepare further populations of beads or pellets containing pharmaceutical active or basic material, an enteric coating layer was applied to the population of beads or pellets containing pharmaceutical active or basic material, (which was previously optionally coated with a separating layer) using an aqueous dispersion of methacrylic acid copolymer plasticized with polyethylene glycol via bottom spraying in a fluid bed. The beads or pellets were dried in a fluid bed apparatus.

Assembly of the capsule was done to contain the following;

one population of pellets or beads containing pharmaceutical active substance designed to begin the release of the active substance in the stomach;

one population of pellets or beads containing basic material designed, to dissolve in the stomach and rapidly increases the pH of the stomach to not less than about 4.5 in less than about one hour;

one population of enteric coated pellets or beads containing pharmaceutical active substance designed to release the active substance between the duodenum and just past the ileocecal junction; and one population of enteric coated pellets or beads containing the basic substance designed to release the basic material in and around the colon in order to maintain a colonic pH of not less than about 4.0.

Example 2

1. This May be Used without Enteric Coat as First Population of Pharmaceutical Active Substance

|  | Formulation 1 (%) wgt | Formulation 2 (%) wgt | Formulation 3 (%) wgt |
|---|---|---|---|
| PPI (proton pump inhibitor) | 15 | 15 | 15 |
| Lactose | 41 | 49 | 53 |
| Starch 1500 | 5 | 5 | — |
| *Hydroxypropyl methyl cellulose | 12 | — | — |
| **Sodium lauryl sulfate | — | — | — |
| Microcrystalline cellulose | 16 | 20 | 20 |
| Silicon dioxide | 1 | 1 | 1 |
| Magnesium stearate | 1 | 1 | 1 |
| ***Methacrylic acid copolymer | — | — | 10 |
| Purified water | QS | — | QS |

*May be replaced or combined with Xanthan gum
**Sodium lauryl sulfate is optional
***Eudragit ™ NE 30 D was used

2. Preparation of Basic Material Loaded Core Material by Extrusion Spheronization This may be used without enteric coat as a population of basic material

|  | Formulation 1 (%) wgt | Formulation 2 (%) wgt | Formulation 3 (%) wgt |
|---|---|---|---|
| Basic | 70 | 71 | 71 |
| Crospovidone | — | 2 | 2 |
| Silicon dioxide | 1 | 1 | 1 |
| Starch 1500 | 5 | — | — |
| Sodium lauryl sulfate | 9 | 10 | 10 |
| Microcrystalline cellulose | 14 | 15 | 15 |
| Magnesium stearate | 1 | 1 | 1 |
| *Purified water | QS | — | QS |

*Between 10% to 100% of the total weight of excipients used is sufficient

3. Preparation of the Optional Separation Layer for a Population of Pharmaceutical Active or Basic Material Loaded Tablets to be Enteric Coated

|  | Formulation (%) wgt |
|---|---|
| *Lustreclear ™ | 9 |
| Purified water | 91 |

*Carrageenan preparation. Use 3% weight gain level

4. Preparation of the Enteric Coating Layer for a Population of the Pharmaceutical Active or Basic Material Loaded Tablets Optionally with Separating Layer

|  | *Formulation (g) |
|---|---|
| Methacrylic acid copolymer | 140 |
| PEG 600 | 28 |
| Talc | 42 |
| Purified water | 500 |

*for coating 2000 g of active loaded tablets optionally covered with separating layer or 2000 g of tablets loaded with basic material Sodium lauryl sulfate was dissolved in purified water and used as the granulation liquid (use of sodium lauryl sulfate is optional). The PPI or basic material was dry mixed with excipients. The dry mix was granulated with aid of granulation liquid in a high shear mixer and the resultant wet granules were dried in a tray dryer oven or fluid bed. The dry granules were milled in a co-mill with screen size of about 1.0 mm. Lubricant was added to the milled granules and then blended in a V-blender. The blended granules were compressed into tablets. Dry granulation was used for formulation 2.

The tablets were optionally coated with separating layer in a side vented coating pan with a Carrageenan/water solution. This is a population of tablets containing pharmaceutical active substance or basic material.

To prepare further populations of tablets containing pharmaceutical active substance or basic material, the enteric coating layer was applied to a portion of the population of tablets containing pharmaceutical active substance or basic material, (which was previously optionally coated with separating layer) using an aqueous dispersion of methacrylic acid copolymer plasticized with polyethylene glycol. The tablets were dried in a coating pan.

Assembly of the multi-functional capsule was done to contain the following:

one population of tablet containing pharmaceutical active substance designed to begin the release of the active substance in the stomach;

one population of tablet containing basic material designed to dissolve in the stomach and rapidly increases the pH of the stomach to not less than about 4.5 in less than about one hour;

one population of enteric coated tablet containing pharmaceutical active substance designed to release the pharmaceutical active substance between the duodenum and just past the ileocecal junction; and one population of enteric coated tablet containing the basic substance designed to release the basic material in and around the colon in order to maintain a colonic pH of not less than about 4.0.

Example 3

1. Preparation of Rapid Release Pharmaceutical Active Loaded Tablets

This may be used without enteric coat as first population of pharmaceutical active substances

|  | Formulation 1 (%) wgt | Formulation 2 (%) wgt | Formulation 3 (%) wgt |
|---|---|---|---|
| PPI (proton pump inhibitor) | 15 | 15 | 15 |
| Lactose | 48 | 49 | 53 |
| Crospovidone | 10 | 5 | — |
| **Sodium lauryl sulfate | — | — | — |
| Microcrystalline cellulose | 16 | 20 | 20 |
| Silicon dioxide | 1 | 1 | 1 |
| Calcium stearate | 1 | 1 | 1 |
| ***Methacrylic acid copolymer | — | — | — |
| Purified water | QS | — | QS |

**Sodium lauryl sulfate is optional
***Between 10% to 100% of the total weight of excipients used is sufficient
QS—quantity sufficient

2. Preparation of Sustained Release Pharmaceutical Active Loaded Tablets

This may be used without enteric coat as second population of pharmaceutical active substances

|  | Formulation 1 (%) wgt | Formulation 2 (%) wgt | Formulation 3 (%) wgt | Formulation 4 (%) wgt |
|---|---|---|---|---|
| PPI (proton pump inhibitor) | 15 | 15 | 15 | 15 |
| Lactose | 43 | 49 | 55.5 | 50.5 |
| Starch 1500 | — | — | — | — |

-continued

|  | Formulation 1 (%) wgt | Formulation 2 (%) wgt | Formulation 3 (%) wgt | Formulation 4 (%) wgt |
|---|---|---|---|---|
| *Hydroxypropyl methyl cellulose | 15 | 10 | 7.5 | — |
| **Sodium lauryl sulfate | — | — | — | — |
| Microcrystalline cellulose | 16 | 15 | 20 | 20 |
| Silicon dioxide | 1 | 1 | 1 | 1 |
| Calcium stearate | 1 | 1 | 1 | 1 |
| ***Methacrylic acid copolymer | — | — | — | 5 |
| Purified water | QS | — | QS | 15 |

*May be replaced or combined with Xanthan gum or hydroxy ethyl cellulose
**Sodium lauryl sulfate is optional
***Eudragit ™ NE 30 D was used
QS—quantity sufficient

3. Preparation of Basic Material Loaded Tablets

This may be used without enteric coat as a first population of basic material

|  | Formulation 1 (%) wgt | Formulation 2 (%) wgt | Formulation 3 (%) wgt |
|---|---|---|---|
| Basic Substance(s) (calcium carbonate) | 70 | 71 | 71 |
| Crospovidone | — | 2 | 2 |
| Silicon Dioxide | 1 | 1 | 1 |
| Starch 1500 | 5 | — | — |
| Sodium lauryl sulfate | 9 | 10 | 10 |
| Microcrystalline cellulose | 14 | 15 | 15 |
| Magnesium Stearate | 1 | 1 | 1 |
| *Purified water | QS | — | QS |

*Between 70% to 100% of the total weight of excipients used is sufficient

4. Preparation of the Optional Separation Layer for Populations of Pharmaceutical Active or Basic Material Loaded Tablets to be Enteric Coated

|  | Formulation (%) wgt |
|---|---|
| *Lustreclear ™ | 9 |
| Purified water | 91 |

*Carrageenan preparation. Use 3% weight gain level

5. Preparation of the Enteric Coating Layer for Population of the Pharmaceutical Active or Basic Material Loaded Tablets Optionally Provided with Separating Layer

|  | *Formulation (g) |
|---|---|
| Methacrylic acid copolymer | 140 |
| PEG 600 | 28 |
| Talc | 42 |
| Purified water | 500 |

*for coating 2000 g of active loaded tablets optionally covered with separating layer or 2000 g of tablets loaded with basic material Sodium lauryl sulfate was dissolved in purified water and used as the granulation liquid (use of sodium lauryl sulfate is optional). The PPI or basic material was dry mixed with excipients and then granulated with the aid of granulation liquid in a high shear mixer. The resultant wet mass was dried in a tray dryer oven or fluid bed to form dry granules. The dry granules were milled in a co-mill equipped with screens with an aperture size of about 1.0 mm. Lubricant was added to the milled granules and blended in a V-blender. The blended granules were then compressed into tablets.

The tablets were optionally covered with separating layer in a side-vented coating pan with a Carrageenan/water solution. This is a population of pharmaceutical active substance or basic material.

If enteric coating is required, an enteric coating is applied to the populations of tablets containing pharmaceutical active or basic material. The enteric coating layer was applied to the population of tablets containing pharmaceutical active or basic material (which was previously optionally coated with a separating layer) using an aqueous dispersion of methacrylic acid copolymer plasticized with polyethylene glycol. The tablets were dried in the coating pan.

Assembly of the capsule was done by encapsulating tablets from the multiple population to obtain a multifunctional oral dosage capsule form containing the following;

one population of tablets containing pharmaceutical active substance designed to begin the rapid release of the active substance in the stomach;

one population of tablets containing basic material designed to dissolve in the stomach and rapidly increases the pH of the stomach to not less than about 4.5 in less than about one hour; and one population of tablets (optionally enteric coated) containing pharmaceutical active substance designed to release the active substance in a sustained manner.

Example 4

This example is directed to a pulsed release capsule that comprises multiple populations of the pharmaceutical active in the form of a rapid release population, a delayed release population and a sustained release population together with multiple populations of a basic substance. Each population is functionally distinct. The capsule provides the release of the pharmaceutical active in a pulsed release manner.

1. Preparation of Rapid Release Pharmaceutical Active Loaded Tablets

This may be used without enteric coat as first population of pharmaceutical active substances

|  | Formulation 1 (%) wgt | Formulation 2 (%) wgt | Formulation 3 (%) wgt |
|---|---|---|---|
| PPI (proton pump inhibitor) | 30 | 30 | 30 |
| Lactose | 28 | 28 | 53 |
| Crospovidone | 10 | 5 | — |
| Sodium Starch glycolate | — | — | 10 |
| Sodium lauryl sulfate | — | 5 | — |
| Microcrystalline cellulose | 30 | 30 | 2 |
| Silicon dioxide | 1 | 1 | 1 |
| Magnesium stearate | 1 | 1 | 1 |

2. Preparation of Delayed Release Pharmaceutical Active Loaded Tablets

The delayed release pharmaceutical active loaded tablets as second population of pharmaceutical active substances were prepared using rapid release pharmaceutical active loaded tablets prepared as above. The rapid release pharmaceutical active loaded tablets were first coated with an over coat of carrageenan, followed by an enteric coat. The formulae of the coats are shown below.

(I) Preparation of the Over Coat Suspension for the Delayed Release Pharmaceutical Active Loaded Tablets

|  | Formulation (%) wgt |
|---|---|
| *Lustreclear ™ | 9 |
| Purified water | 91 |

*Carrageenan preparation. Used 3% weight gain level (II) Preparation of the Enteric Coat Pseudolatex Suspension for the Delayed Release Pharmaceutical Active Loaded Tablets

|  | *Formulation (g) |
|---|---|
| *Cellulose acetate phthalate (Aquacoat CPD ™) | 506 |
| Diethyl phthalate | 36.44 |
| Purified water | 712.4 |

*for coating 2000 g of active loaded tablets optionally covered with separating layer or 2000 g of tablets. The quantity of Aquacoat used contained 151.8 g of cellulose acetate phthalate.

3. Preparation of Sustained Release Pharmaceutical Active Loaded Tablets

This may be used without enteric coat as third population of pharmaceutical active substances

|  | Formulation 1 (%) wgt | Formulation 2 (%) wgt | Formulation 3 (%) wgt | Formulation 4 (%) wgt |
|---|---|---|---|---|
| PPI (proton pump inhibitor) | 30 | 30 | 30 | 30 |
| Lactose | 30 | 30 | 30 | 30 |
| Crospovidone | 5 | 5 | — | — |
| *Hydroxypropyl methyl cellulose | 12 | 0-12 | 0-12 | 0-12 |
| Pectin | 0-10 | 10 | 0-10 | 0-10 |
| Xanthan Gum | 0-10 | 0-10 | 7 | 0-10 |
| Carbomer | 0-10 | 0-10 | 0-10 | 7 |
| Microcrystalline cellulose | 16 | 20 | 20 | 20 |
| Silicon dioxide | 1 | 1 | 1 | 1 |
| Magnesium stearate | 1 | 1 | 1 | 1 |

*May be replaced or combined with ethylcellulose and or hydroxyethyl cellulose
Prepared by direct compression

4. Preparation of Basic Material Loaded Tablets

This may be used with or without an enteric coat as a first population of basic material or granulated with ethylcellulose to impart a sustained release effect. An enteric coat impacts a delayed release effect.

|  | Formulation 1 (%) wgt | Formulation 2 (%) wgt | Formulation 3 (%) wgt |
|---|---|---|---|
| Basic | 70 | 71 | 71 |
| Crospovidone | — | 2 | 2 |
| Silicon dioxide | 1 | 1 | 1 |
| Starch 1500 | 5 | — | — |
| Sodium lauryl sulfate | 9 | 10 | 10 |
| Microcrystalline cellulose | 14 | 15 | 15 |
| Magnesium stearate | 1 | 1 | 1 |
| *Purified water | QS | — | QS |

May be prepared by direct compression or by wet granulation.
*Between 10% to 100% of the total weight of excipients used is sufficient.

Sodium lauryl sulfate was dissolved in purified water and used as the granulation liquid (use of sodium lauryl sulfate is optional). The PPI or basic material was dry mixed with excipients. The dry mix was granulated with aid of granulation liquid in a high shear mixer and the resultant wet granules were dried in a tray dryer oven or fluid bed. The dry granules were milled in a co-mill with screen size of about 1.0 mm. Lubricant was added to the milled granules and then blended in a V-blender. The blended granules were compressed into tablets.

The tablets were optionally coated with separating layer in a side vented coating pan with a Carrageenan/water solution. This is a population of tablets containing pharmaceutical active substance or basic material.

If enteric coating is required, an enteric coating is applied to the populations of tablets containing pharmaceutical active or basic material. The enteric coating layer was applied to the population of tablets containing pharmaceutical active or basic material (which was previously optionally coated with a separating layer) using an aqueous dispersion of methacrylic acid copolymer plasticized with polyethylene glycol. The tablets were dried in the coating pan.

Assembly of the capsule was done by encapsulating tablets from the multiple population to obtain a multifunctional oral dosage capsule form containing the following;

one population of tablets containing pharmaceutical active substance designed to begin the rapid release of the active substance in the stomach;

one population of tablets (optionally enteric coated) containing pharmaceutical active substance designed to release the active substance in a sustained manner;

one population of tablets containing pharmaceutical active substance designed to release the active substance in a delayed manner; and one population of tablets containing basic material designed to release the basic material in a rapid, sustained or delayed manner.

Although certain embodiments have been described herein in detail it is understood by those of skill in the art that using no more than routine experimentation, many equivalents to the specific embodiments of the invention described herein can be made. Such equivalents are intended to be encompassed by the scope of the claims appended hereto.

The invention claimed is:

1. A method for treating conditions caused by inappropriate gastric acid secretion, said method comprising administering an oral pharmaceutical composition to a subject in need of such treatment, wherein the composition comprising at least three separate and distinct populations of at least one of beads, pellets, tablets and granules provided in a capsule, the at least three separate and distinct populations comprising:
   (i) a first population of a pharmaceutical active comprising a pharmaceutical active substance releasable at a first rate, wherein the first population is selected from the group consisting of: a population of beads, a population of pellets, a population of tablets, a population of granules, and any combination thereof;
   (ii) a second population of a pharmaceutical active comprising a pharmaceutical active substance releasable at a second rate, wherein the second population is selected from the group consisting of: a population of beads, a population of pellets, a population of tablets, a population of granules, and any combination thereof;
   (iii) a population of a basic substance, wherein the population of the basic substance excludes said pharmaceutical active substance, the population of the basic substance being selected from the group consisting of: a population of beads, a population of pellets, a population of tablets, a population of granules, and any combination thereof; and
   further comprising (iv) a population of a basic substance, wherein the basic substance is released slower than the basic substance of (ii), wherein the basic substance of (iv) further comprises an enteric coating, wherein a separating layer is provided to separate the basic substance of (iv) from contact with the enteric coating.

2. The method of claim 1, wherein said inappropriate gastric acid secretion is night time acid secretion and said administration is done at night time.

3. The method of claim 1, wherein the first rate of release is faster than the second rate of release.

4. The method of claim 1, wherein the second rate of release is release in at least one of a delayed and sustained manner.

5. The method of claim 1, wherein the oral pharmaceutical composition further comprises a third population of a pharmaceutical active comprising a pharmaceutical active substance being releasable at a third rate.

6. The method of claim 5, wherein the first rate of release is a release in a rapid manner, the second rate of release is release in at least one of a delayed and sustained manner, and the third rate of release is release in at least one of a delayed and sustained manner.

7. The method of claim 1, wherein the oral pharmaceutical composition is a pulsed release capsule.

8. The method of claim 1, wherein at least one of (i), (ii) and (iii) further comprise at least one excipient.

9. The method of claim 8, wherein said at least one excipient is selected from the group consisting of binders, surfactants, fillers, lubricants, disintegrating agents, sustained release agents, and combinations thereof.

10. The method of claim 8, wherein said at least one excipient of (i) to (iii) is present in an amount of about 0.5% to about 95% by weight of said beads, pellets, tablets or granules of said population.

11. The method of claim 8, wherein said at least one excipient of (iii) is a sustained release agent.

12. The method of claim 8, wherein said at least one excipient of (i) serves to release the pharmaceutical active substance of the first population faster than the pharmaceutical active substance of the second population.

13. The method of claim 12, wherein said at least one excipient of (i) is a disintegrating agent.

14. The method of claim 1, wherein the pharmaceutical active of (iii) further comprises an enteric coating.

15. The method of claim 14, wherein a separating layer is provided to separate the pharmaceutical active of (iii) from contact with the enteric coating.

16. The method of claim 1, wherein the pharmaceutical active substance of the first population is the same as the pharmaceutical active substance of the second population.

17. The method of claim 1, wherein at least one of the pharmaceutical active substances of (i) and (iii) comprises an acid labile drug.

18. The method of claim 17, wherein said at least one of the pharmaceutical active substances of (i) and (iii) comprises at least one of a proton pump inhibitor, a prodrug of a proton pump inhibitor, a single enantiomer of a proton pump inhibitor, a single enantiomer of a prodrug of a proton pump inhibitor, and combinations thereof.

19. The method of claim 1, wherein said basic substance is selected from the group consisting of sodium, potassium, calcium, magnesium and aluminum salts of phosphoric acid, carbonic acid, and citric acid; aluminum hydroxide; sodium bicarbonate; aluminum, calcium and magnesium hydroxides; magnesium oxide; trihydroxymethylaminomethane; basic amino acids or their salts; and mixtures thereof.

20. The method of claim 1, wherein (i) provides delivery of the pharmaceutical active to the stomach upon oral administration.

21. The method of claim 1, wherein (iii) provides delivery of the pharmaceutical active between the duodenum and just past the ileocecal junction.

22. The method of claim 1, wherein (ii) is rapidly released in the stomach and increases the stomach pH to more than about 4 and less than about 7 in less than about 1 hour, wherein the pharmaceutical active of (i) is rapidly or gradually released in the stomach.

23. The method of claim 14, wherein (ii) is rapidly released in the stomach and increases the stomach pH to more than about 4 and less than about 7 in less than about 1 hour, wherein the pharmaceutical active of (i) is rapidly or gradually released in the stomach.

24. The method of claim 1, wherein (ii) is rapidly released in the stomach and increases the stomach pH to more than about 4 and less than about 7 in less than about 1 hour, wherein the pharmaceutical active of (i) is rapidly or gradually released in the stomach, (iii) provides delivery of the pharmaceutical active between the duodenum and just past the ileocecal junction, and (iv) releases said basic substance just past the ileocecal junction.

25. The method of claim 9, wherein said sustained release agents are selected from the group consisting of pectin, polyvinyl alcohol, polyvinyl acetate, hydroxypropyl cellulose, methylcellulose, ethylcellulose, hydroxypropyl methylcellulose, carrageenan, xanthan gum, carbomer and mixtures thereof.

26. The method of claim 9, wherein said disintegrating agents are selected from the group consisting of homopolymer cross-linked N-vinyl-2-pyrrolidone, sodium starch glycolate, cross-linked sodium carboxymethylcellulose and mixtures thereof.

27. A method for treating conditions caused by inappropriate gastric acid secretion, said method comprising administering an oral pharmaceutical composition to a subject in need of such treatment, the composition comprising at least three separate and distinct populations of at least one of beads, pellets, tablets and granules provided in a capsule, the at least three separate and distinct populations comprising:
 (i) a population of a pharmaceutical active, wherein the population of the pharmaceutical active is selected from the group consisting of: a population of beads, a population of pellets, a population of tablets, a population of granules, and any combination thereof;
 (ii) a population of enteric coated pharmaceutical active, wherein the population of enteric coated pharmaceutical active is selected from the group consisting of: a population of beads, a population of pellets, a population of tablets, a population of granules, and any combination thereof;
 (iii) a population of a basic substance, wherein the population of the basic substance excludes said pharmaceutical active, the population of the basic substance being selected from the group consisting of: a population of beads, a population of pellets, a population of tablets, a population of granules, and any combination thereof; and
 (iv) a population of enteric coated basic substance, wherein the population of enteric coated basic substance excludes said pharmaceutical active, the population of enteric coated basic substance being selected from the group consisting of: a population of beads, a population of pellets, a population of tablets, a population of granules, and any combination thereof.

28. The method of claim 27, wherein a separating layer is provided to said population of enteric coated pharmaceutical active, said separating layer being provided to separate said pharmaceutical active from contact with said enteric coating.

29. The method of claim 27, wherein a separating layer is provided to said population of enteric coated basic substance, said separating layer being provided to separate said basic substance from contact with said enteric coating.

30. The method of claim 27, wherein at least one excipient is provided to at least one of (i) to (iv).

31. The method of claim 30, wherein said at least one excipient is selected from the group consisting of binders, surfactants, fillers, lubricants, disintegrating agents, sustained release agents, and combinations thereof.

32. The method of claim 30, wherein said at least one excipient is present in an amount of about 0.5% to about 95% by weight of said beads, pellets, tablets or granules of said population.

33. The method of claim 27, wherein at least one overcoating layer is provided to at least one of said population of (i) to (iv).

34. The method of claim 27, wherein said pharmaceutical active comprises an acid labile drug.

35. The method of claim 34, wherein said pharmaceutical active comprises a proton pump inhibitor, a prodrug of a proton pump inhibitor, a single enantiomer of a proton pump inhibitor, a single enantiomer of a prodrug of a proton pump inhibitor, and combinations thereof.

36. The method of claim 27, wherein said basic substance is selected from the group consisting of sodium, potassium, calcium, magnesium and aluminum salts of phosphoric acid, carbonic acid, and citric acid; aluminum hydroxide; sodium bicarbonate; aluminum, calcium and magnesium hydroxides; magnesium oxide; trihydroxymethylaminomethane; basic amino acids or their salts; and mixtures thereof.

37. The method of claim 36, wherein said basic substance is calcium carbonate.

38. The method of claim 27, wherein said population of any one of (i) to (iv) is made by extrusion spheronization or compression into tablets.

39. The method of claim 27, wherein (i) begins delivery of said active in the stomach upon oral administration.

40. The method of claim 27, wherein (i) provides delivery of said active to the stomach, (iii) provides delivery of said active between the duodenum and just past the ileocecal junction and (iv) provides delivery of said active to the ascending, transverse and descending colon.

41. The method of claim 27, wherein (ii) is rapidly released in the stomach and increases the stomach pH to more than about 4 and less than about 7 in less than 1 hour, wherein (i) is rapidly or gradually released in the stomach, (iii) provides rapid or gradual release of active between the duodenum and just past the ileocecal junction and (iv) releases said basic substance just past the ileocecal junction.

\* \* \* \* \*